(12) United States Patent
Yu et al.

(10) Patent No.: US 10,139,343 B2
(45) Date of Patent: Nov. 27, 2018

(54) METHOD AND APPARATUS FOR CHEMILUMINESCENCE AND/OR FLUORESCENCE MEASURING

(71) Applicant: Technogenetics Holdings S.r.l., Milan (IT)

(72) Inventors: Chao Yu, Shanghai (CN); Jianbo Tang, Chengdu (CN); Shenguang Su, Shenzhen (CN); Qingwen Tang, Putian (CN); Luca Melillo, Lioni (IT)

(73) Assignee: Technogenetics Holdings S.r.l., Milan (IT)

( * ) Notice: Subject to any disclaimer, the term of this patent is extended or adjusted under 35 U.S.C. 154(b) by 0 days.

(21) Appl. No.: 15/326,654

(22) PCT Filed: Jul. 21, 2015

(86) PCT No.: PCT/EP2015/066618
§ 371 (c)(1),
(2) Date: Jan. 17, 2017

(87) PCT Pub. No.: WO2016/012434
PCT Pub. Date: Jan. 28, 2016

(65) Prior Publication Data
US 2017/0191936 A1 Jul. 6, 2017

(30) Foreign Application Priority Data
Jul. 21, 2014 (CN) .......................... 2014 1 0348068

(51) Int. Cl.
*G01N 21/13* (2006.01)
*G01N 21/64* (2006.01)
(Continued)

(52) U.S. Cl.
CPC ......... *G01N 21/6428* (2013.01); *G01N 21/13* (2013.01); *G01N 21/645* (2013.01);
(Continued)

(58) Field of Classification Search
CPC .... G01N 21/6428; G01N 21/64; G01N 21/63; G01N 21/13; G01N 21/01; G01N 21/76; G01N 21/645
(Continued)

(56) References Cited

U.S. PATENT DOCUMENTS 5,173,741 A 12/1992 Wakatake
5,223,218 A 6/1993 Fukuoka et al.
(Continued)

FOREIGN PATENT DOCUMENTS

JP 2002-308429 * 10/2002 ............. B65G 57/03
WO WO 2016/012434 1/2016

OTHER PUBLICATIONS

Tomoharu et al, English Machine Translation of JP 2002-308429 A, Container Group Hanging Holding Device and Container Hanging Holding Method, Oct. 23, 2002, Translation obtained on Jan. 18, 2018, p. 1-14 (Year: 2002).*
(Continued)

*Primary Examiner* — Christine T Mui

(57) ABSTRACT

A fluorescence and/or chemiluminescence measuring device and method, able to achieve a series of actions synchronously including placing reaction cup, injection, extraction, reading, releasing reaction cup and light block, and no extra arm for getting and releasing reaction cup is needed. A sliding cartridge drives the reaction cup to perform movement to achieve the actions above in turn. Moreover, it maximally ensures a consistence of distance and relative height between each reaction cup and the reading photomultiplier device, so as the operation speed is faster and easier.

10 Claims, 17 Drawing Sheets

(51) Int. Cl.
  *G01N 21/76* (2006.01)
  *G01N 21/11* (2006.01)
  *G01N 35/10* (2006.01)
  *G01N 21/01* (2006.01)
  *G01N 35/04* (2006.01)

(52) U.S. Cl.
  CPC ............ *G01N 21/76* (2013.01); *G01N 21/11* (2013.01); *G01N 35/10* (2013.01); *G01N 2021/0187* (2013.01); *G01N 2035/0475* (2013.01); *G01N 2201/068* (2013.01)

(58) Field of Classification Search
  USPC ........ 436/54; 422/50, 52, 82.07, 68.1, 82.05
  See application file for complete search history.

(56) References Cited

U.S. PATENT DOCUMENTS

| | | | | |
|---|---|---|---|---|
| 8,143,065 | B2* | 3/2012 | Tanaka | G01N 35/026 436/43 |
| 8,318,499 | B2* | 11/2012 | Fritchie | G01N 35/00732 436/43 |
| 2011/0256630 | A1 | 10/2011 | Clinton | |

OTHER PUBLICATIONS

International Search Report and the Written Opinion dated Oct. 7, 2015 From the International Searching Authority Re. Application No. PCT/EP2015/066618.

\* cited by examiner

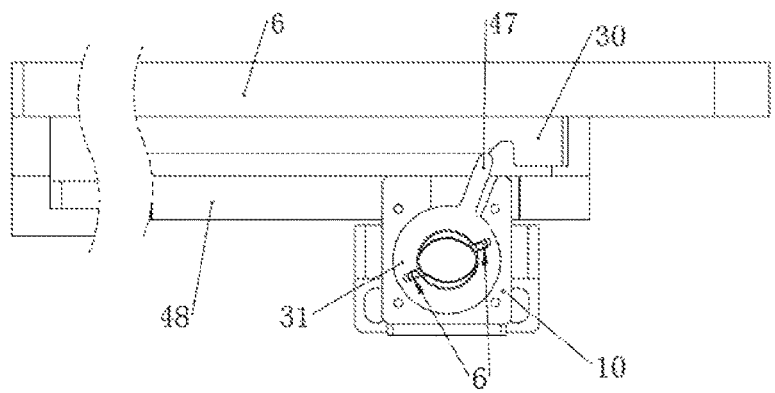
FIG. 17'
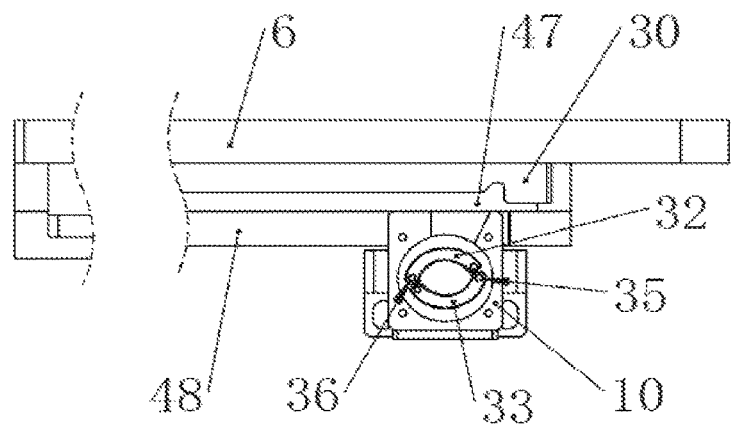
FIG. 17"
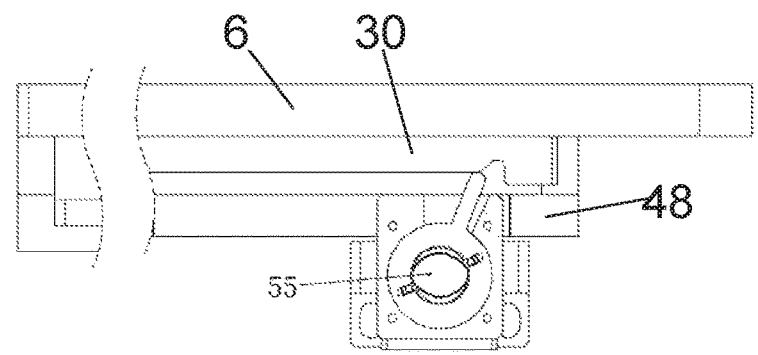
FIG. 18'
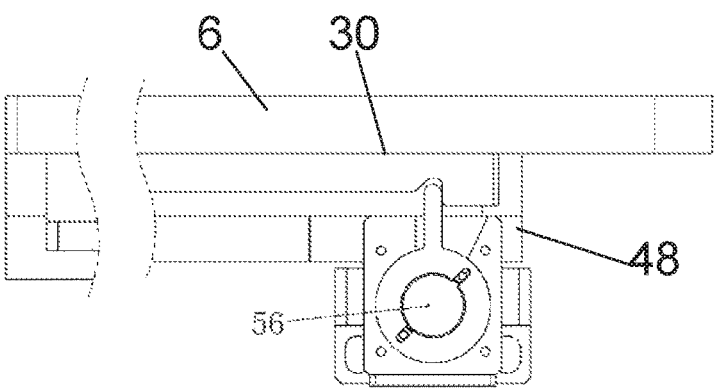
FIG. 18"

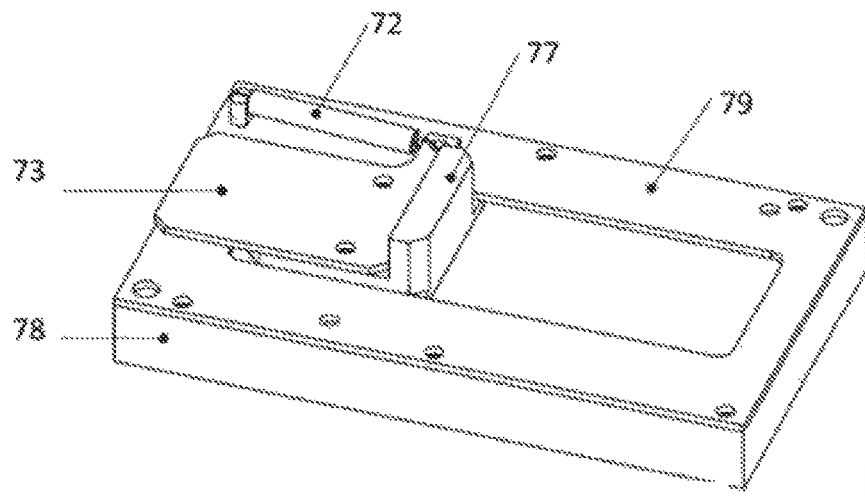
FIG. 19'
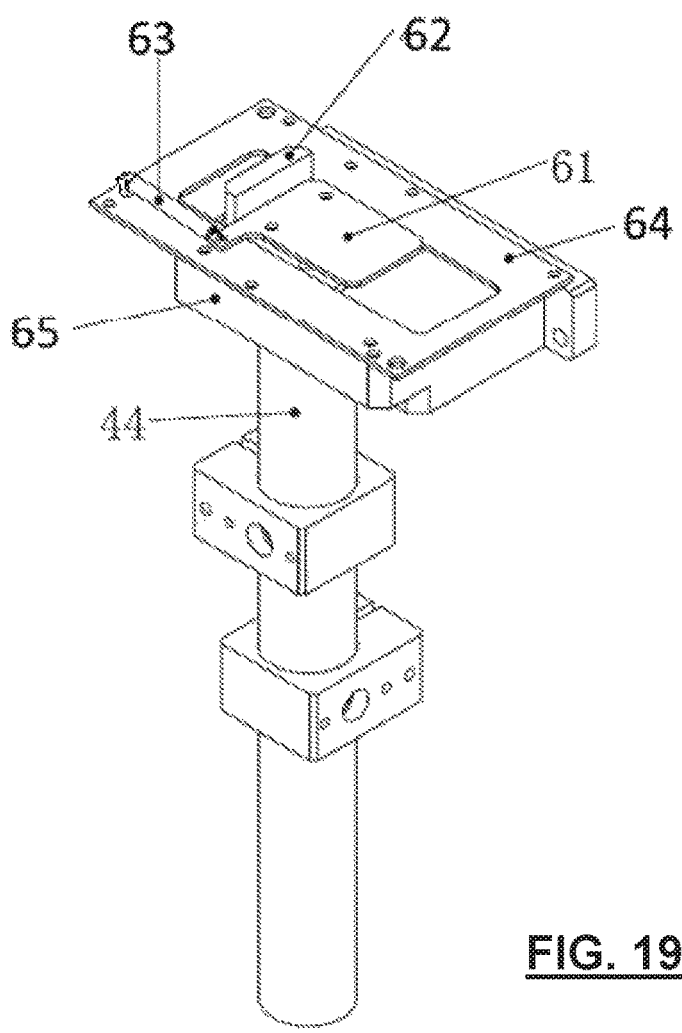
FIG. 19"

FIG. 20"

METHOD AND APPARATUS FOR CHEMILUMINESCENCE AND/OR FLUORESCENCE MEASURING

RELATED APPLICATIONS

This application is a National Phase of PCT Patent Application No. PCT/EP2015/066618 having International filing date of Jul. 21, 2015, which claims the benefit of priority of Chinese Patent Application No. 201410348068.9 filed on Jul. 21, 2014. The contents of the above applications are all incorporated by reference as if fully set forth herein in their entirety.

FIELD AND BACKGROUND OF THE INVENTION

The present invention relates to a method and apparatus for chemiluminescence and/or fluorescence measuring.

At present, fluorescence or chemiluminescence measuring instruments generally use reading modules. The fluorescent measuring device measures fluorescence from a reaction cup containing injection liquid; the device needs to place a reaction cup containing inject liquid, read indication and drop reaction cup; placing reaction cup and dropping reaction cup are not completed in the same mechanism, but an extra reaction cup dropping arm is needed, and that makes the structure complicated and more time and cost consuming. Injection and reading cannot be completed synchronously, a delay for reading is needed after injection. There is no ideal control on distance between the reading device (normally a photomultiplier) and the reaction cup, and thus reading quality is lowered.

Therefore there is a need to ensure the correct operation of the device by increasing efficiency and ensuring easiness of use.

SUMMARY OF THE INVENTION

Therefore it is the main object of the present invention to provide a method and apparatus for chemiluminescence and/or fluorescence measuring, which overcomes the above problems/drawbacks.

In the framework of the present description, the method and apparatus of the invention is applicable to either fluorescence or chemiluminescence measuring or both, therefore reference to fluorescence and/or chemiluminescence is to be understood as involving equivalent basic considerations.

The primary aim of the present invention is to provide a new type of fluorescence and/or chemiluminescence measuring device and method, able to achieve a series of actions synchronously including placing reaction cup, injection, extraction, reading, releasing reaction cup and light block, and no extra arm for getting and releasing reaction cup is needed. A sliding cartridge drives the reaction cup to perform movement to achieve the actions above in turn. Moreover, it maximally ensures a consistence of distance and relative height between each reaction cup and the reading device (photomultiplier), so as the operation speed is faster and easier.

An object of the present invention is an apparatus configured for chemiluminescence and/or fluorescence measuring, comprising a photomultiplier device receiving and measuring a photo-emission of a reaction cup, characterized in that it comprises, according to claim 1:

a reading unit module comprising said photomultiplier device, configured to read said chemiluminescence and/or fluorescence emitted by said reaction cup;

a sliding cartridge module, configured to contain said reaction cup, also configured to slide in a first sliding direction;

a first sliding arrangement configured to let said sliding cartridge module slide according to said first sliding direction and to stop said sliding cartridge module to locate said reaction cup in turn at a reaction cup placing position, a reading and injector position, a liquid extraction position and a reaction cup releasing position;

an injector module, configured to slide in a second sliding direction substantially perpendicular to said first sliding direction;

a second sliding arrangement configured to let said injector module slide according to said second sliding direction, to inject reaction agents into said reagent cup when said sliding cartridge module is in said reading and injector position, and to extract liquid from said reagent cup when said sliding cartridge module is in said liquid extraction position;

a shifting fork module, configured to hold said reaction cup in said sliding cartridge module or let said reaction cup drop from said sliding cartridge module when in said reaction cup releasing position;

a shield module configured to envelope said apparatus completely, and comprising a first hole to let said reaction cup enter said sliding cartridge module when in said reaction cup placing position, and a second hole to let said reaction cup drop when said sliding cartridge module is in said reaction cup releasing position;

a light block module, configured to close said first and second hole when said sliding cartridge module is neither in said reaction cup placing position nor in said reaction cup releasing position.

Another object of the present invention is a method for chemiluminescence and/or fluorescence measuring using said apparatus.

It is a particular object of the present invention an apparatus and method for chemiluminescence and/or fluorescence measuring, as described in the attached claims, which are considered an integral part of the present description.

BRIEF DESCRIPTION OF THE SEVERAL VIEWS OF THE DRAWINGS

The invention will become fully clear from the following detailed description, given by way of a mere exemplifying and non-limiting example, also with reference to the attached drawing figures, wherein:

FIG. 17' is a first illustration of the shifting fork mechanism of the second embodiment example;

FIG. 17" is a second illustration of the shifting fork mechanism of the second embodiment example;

FIG. 18' is an illustration when the shifting fork supports the reaction cup of the second embodiment example;

FIG. 18" is an illustration of the shifting fork to drop reaction cup of the second embodiment example;

FIGS. 19', 19" show the structure of the light block mechanism of the cup release hole of the second embodiment example;

The same reference numerals and letters in the figures designate the same or functionally equivalent parts.

DESCRIPTION OF SPECIFIC EMBODIMENTS OF THE INVENTION

Figure 1:
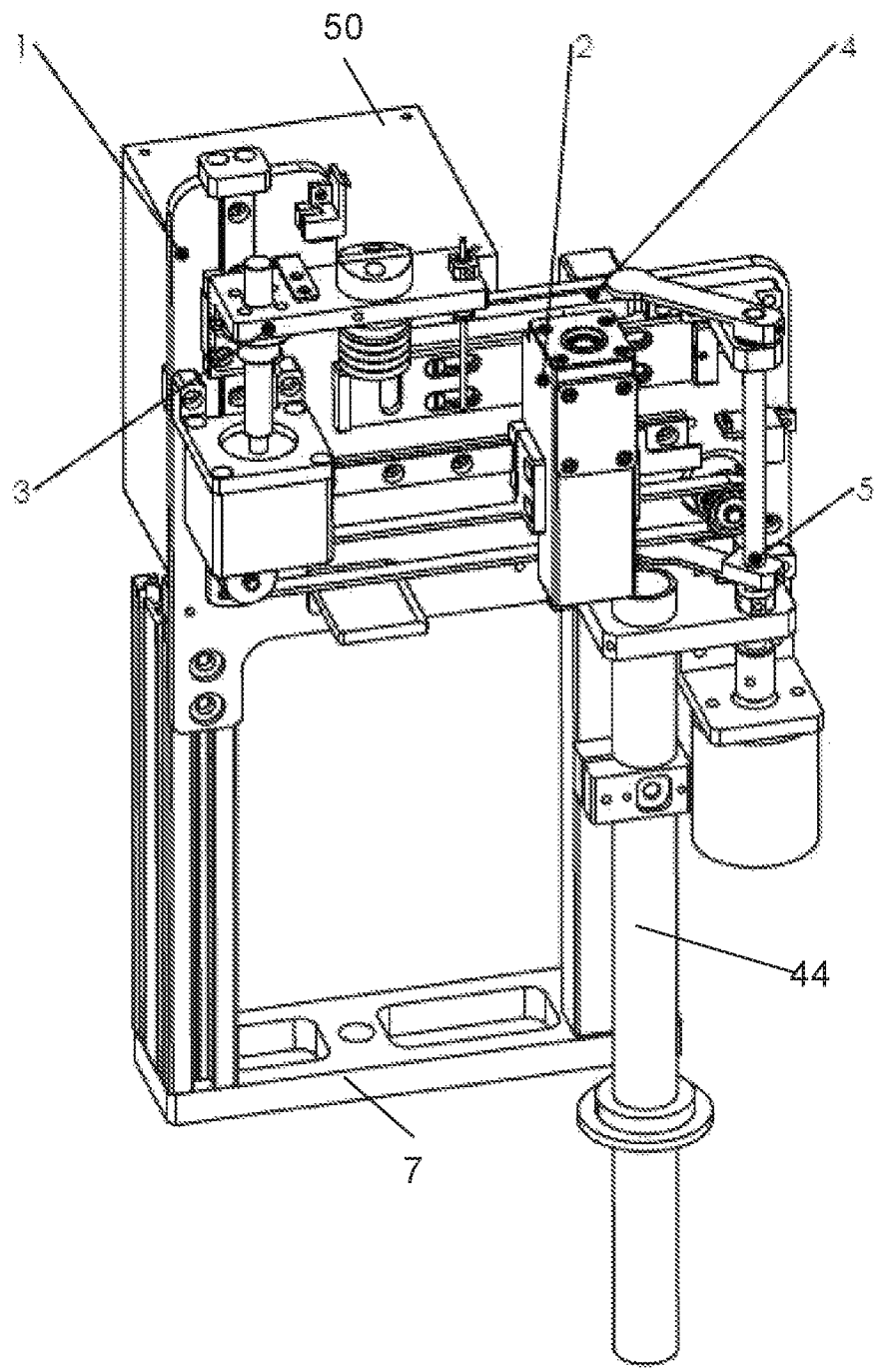
FIG. 1 shows a first embodiment example of internal structure of the device of this invention.
Figure 2:
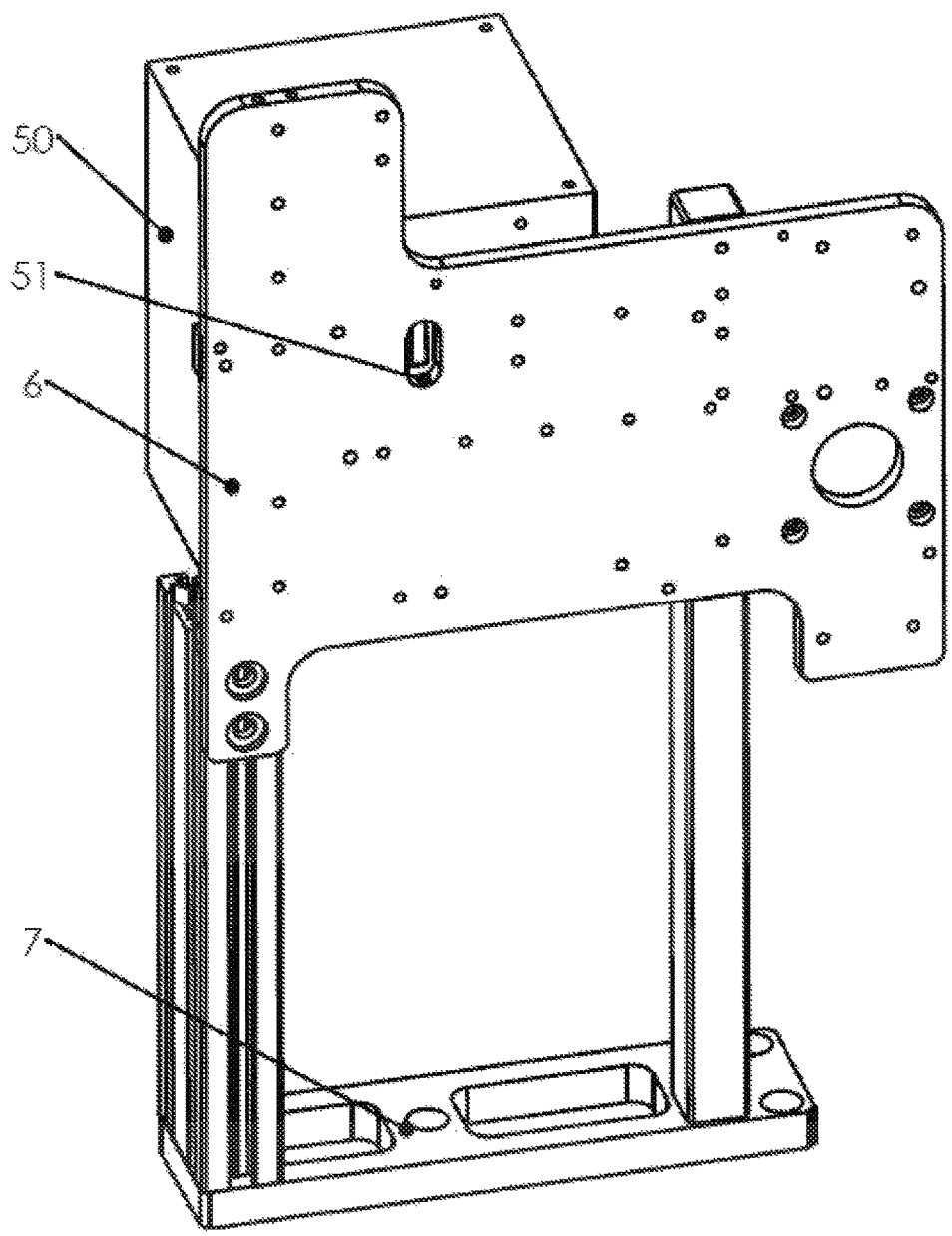
FIG. 2 shows installation of the photomultiplier of the first embodiment example.

With reference to the FIGS. 1-11, a fluorescence and/or chemiluminescence measuring device of the invention, according to a first non-limiting embodiment example, basically comprises the following modules:

reading unit module 1, sliding cartridge module 2 with corresponding sliding arrangement, injector module 3 with corresponding sliding arrangement, shifting fork module 4, light block module 5, frame and shield 57.

The reading unit module 1, sliding cartridge module 2 with corresponding sliding arrangement, injector module 3 with corresponding sliding arrangement, shifting fork module 4, light block module 5 and frame are all placed in the shield 57.

The frame comprises fixation vertical plate 6 and supporting base 7 used for installing the fixation vertical plate.

Embodiment particulars are illustrated in the following.

The sliding cartridge module 2 is driven by a timing belt 15 and a step motor 13 to move leftward and rightward to locate the reaction cup 12 in turn at reaction cup placing position, reading and injector position, liquid extraction position and reaction cup releasing position by movements through a linear slider 8 and a sliding cartridge 2.

When the sliding cartridge module 2 is at the reaction cup placing position (right side position in FIG. 1), the reaction cup 12 is placed into sliding cartridge unit 10 of the sliding cartridge 2.

The injector module 3 injects liquid into the reaction cup 12 in the sliding cartridge module 2 at the position of the reading and injector position (rightmost position, in correspondence of the injection head 26). Then the liquid is extracted from the reaction cup in the sliding cartridge module 2 at the liquid extraction position (intermediate position, in correspondence of the extraction needle 28).

Photomultiplier 50 is a component of a known type able to measure and count the photon emission by the reaction cup.

Photomultiplier 50 of the reading unit 1 is fixed on the fixation vertical plate 6 of the frame. Through light hole 51 in the fixation vertical plate, it receives optical signal emitted from the reaction cup at the reading and injector position.

The shifting fork module 4 is used to support the reaction cup by clamping tightly a first rotary paddle 32 and a second rotary paddle 33 connected to ring fork 31. When the linear sliding cartridge moves to the position of reaction cup releasing (FIG. 9, right side position, FIGS. 1, 9), the ring fork 31 rotates to drive the rotary paddle 47 to move, as the paddle engages in a recess 30" of the sliding notched plate 30. When aperture between them gets larger, the reaction cup will automatically drop down, preferably in the cup releasing tube 44.

The light block module 5 (details with reference to FIG. 10) controls rotation position of the light barrier of the reaction cup releasing hole and reaction cup placing hole due to driving of a motor: it will respectively block the reaction cup placing hole and the reaction cup dripping hole.

Two light barriers are fixed on motor axis. Motor axis drives the block sheets rotate, open or close the only two openings (placing reaction cup and drop reaction cup) of the whole device to make the device form a closed space.

The light barriers are used for preventing outside light from coming into the device, and thus make the device form a dark room, thanks primarily to the shield 57 which envelops the apparatus completely. That maximally lowers background noise of the outside to reading.

The whole reading module of the device is wrapped by light-proof overall shield 57, with only reaction cup placing hole 52 and reaction cup releasing hole 53 for placing the reaction cup to be measured from the upside, or releasing the reaction cup measured from the downside (FIG. 11); the light block mechanism 5 is used for blocking the reaction cup placing hole and reaction cup releasing hole to prevent outside light from coming into the module during reading measuring period.

Figure 3:
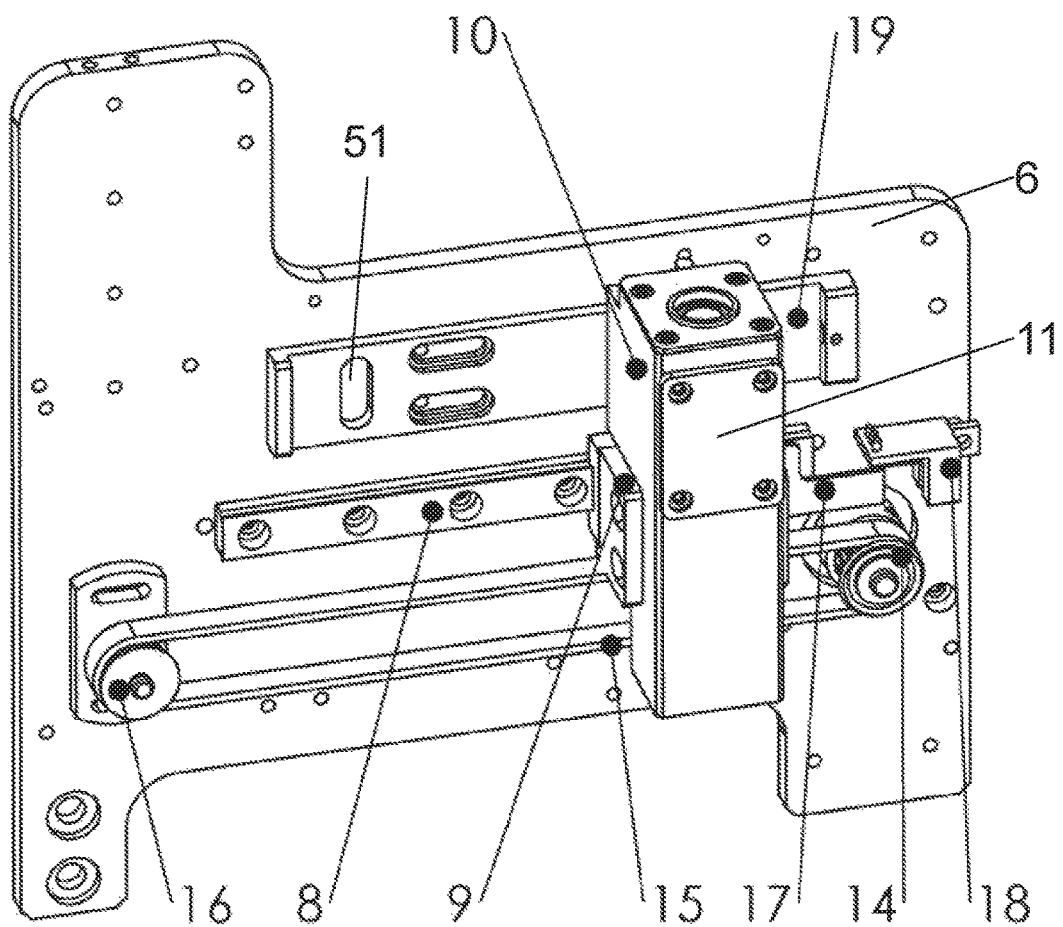
FIG. 3 shows structure of the linear sliding cartridge mechanism of the first embodiment example.
Figure 4:
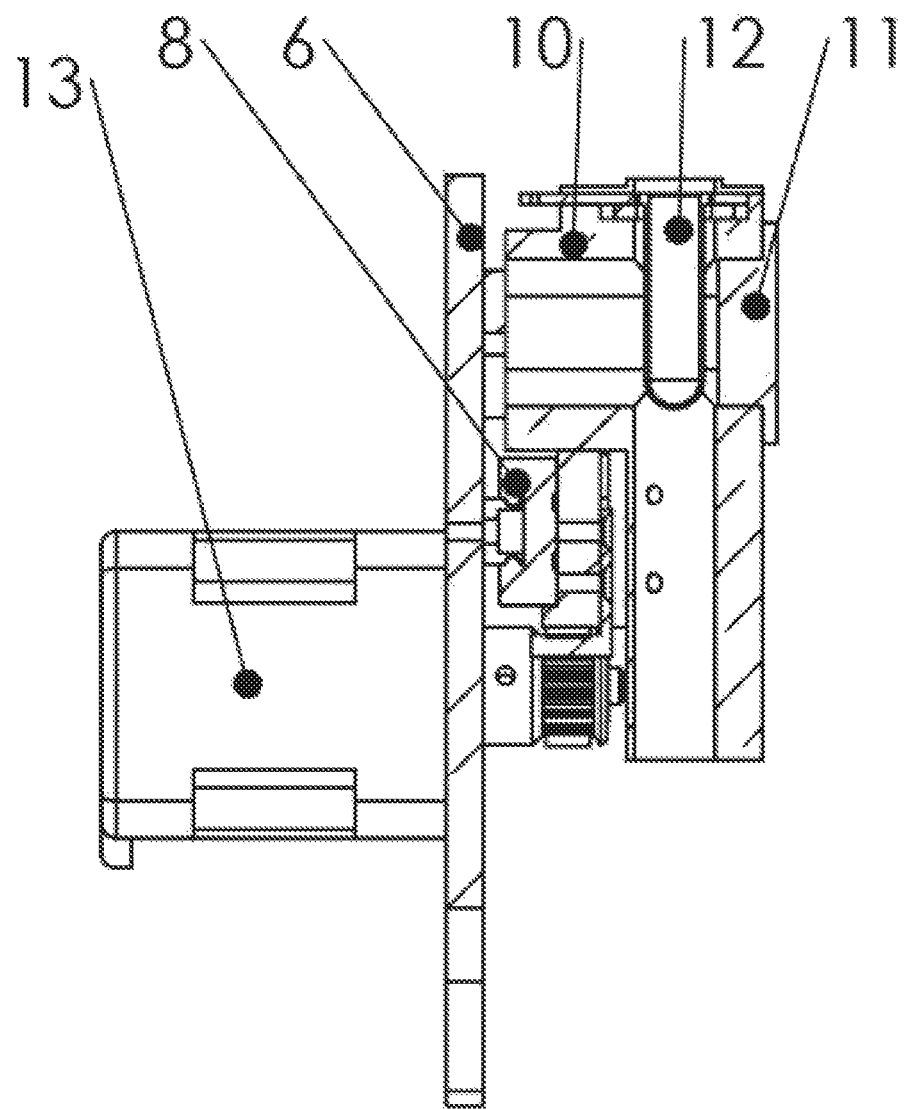
FIG. 4 is a right view of the linear sliding cartridge mechanism of the first embodiment example.

With particular reference to FIGS. 3 and 4, the linear sliding cartridge module 2 comprises a linear slider 8, fixation base 9, sliding cartridge 10, reflector 11, a step motor 13, timing belt pulley 14, timing belt 15, tensioning pulley 16, horizontal home inducer 17, a home sensor 18 and photomultiplier light barrier 19. The reaction cup 12 is placed inside the sliding cartridge 10.

The sliding cartridge 10 slides on the linear slider 8 with the fixation seat 9, and is installed on front side of the fixation vertical plate 6. The front side of the sliding cartridge 10 is equipped with an emission reflector 11, the reaction cup 12 is placed inside the sliding cartridge 10, and a reaction cup dripping duct 44 is equipped at lower part of the sliding cartridge, to let the reaction cup drop down.

The timing belt pulley 14 and the tensioning pulley 16 are both fixed on the fixation vertical plate 6 and are installed in a substantial horizontal direction on lower part of the linear slider 8; the step motor 13 is fixed on the back of the fixation vertical plate 6 to drive the timing belt pulley 14 after passing through the fixation vertical plate 6; the timing belt 15 rolls around the timing belt pulley 14 and the tensioning pulley 16 for tension adjustment of the timing belt.

The timing belt 15 connects with the fixation seat 9. The sliding cartridge 10 is put on the timing belt 15 with the fixation seat 9 and performs linear reciprocating motion along with and moved by the timing belt 15.

When the horizontal home sensor 17 installed on the fixation set contacts with the home sensor 18 that is installed on the fixation vertical plate 6 and horizontally in parallel with the linear sliding rail, the home signal is triggered and reaction cup dropping home position of the sliding cartridge 10 is confirmed.

When the driving linear sliding cartridge moves to the rightmost side, the horizontal home sensor 17 fixed on the fixation seat of the linear sliding cartridge contacts with the home sensor 18 fixed on the fixation vertical plate 6 and at horizontal level of the linear sliding rail, the home signal is triggered, and thus home position of the linear sliding cartridge is found; the motor 13 controls movement position of the linear sliding cartridge 10.

The linear slider 8 ensures consistence of the distance between the sliding cartridge module 2 and the fixation vertical plate 6 during movement. Because the photomultiplier (PMT) 50 is fixed on the fixation vertical plate, thus consistent distance between the reaction cup and the PMT in the sliding cartridge is ensured, and therefore reading consistence is maximally enhanced.

Figure 5:
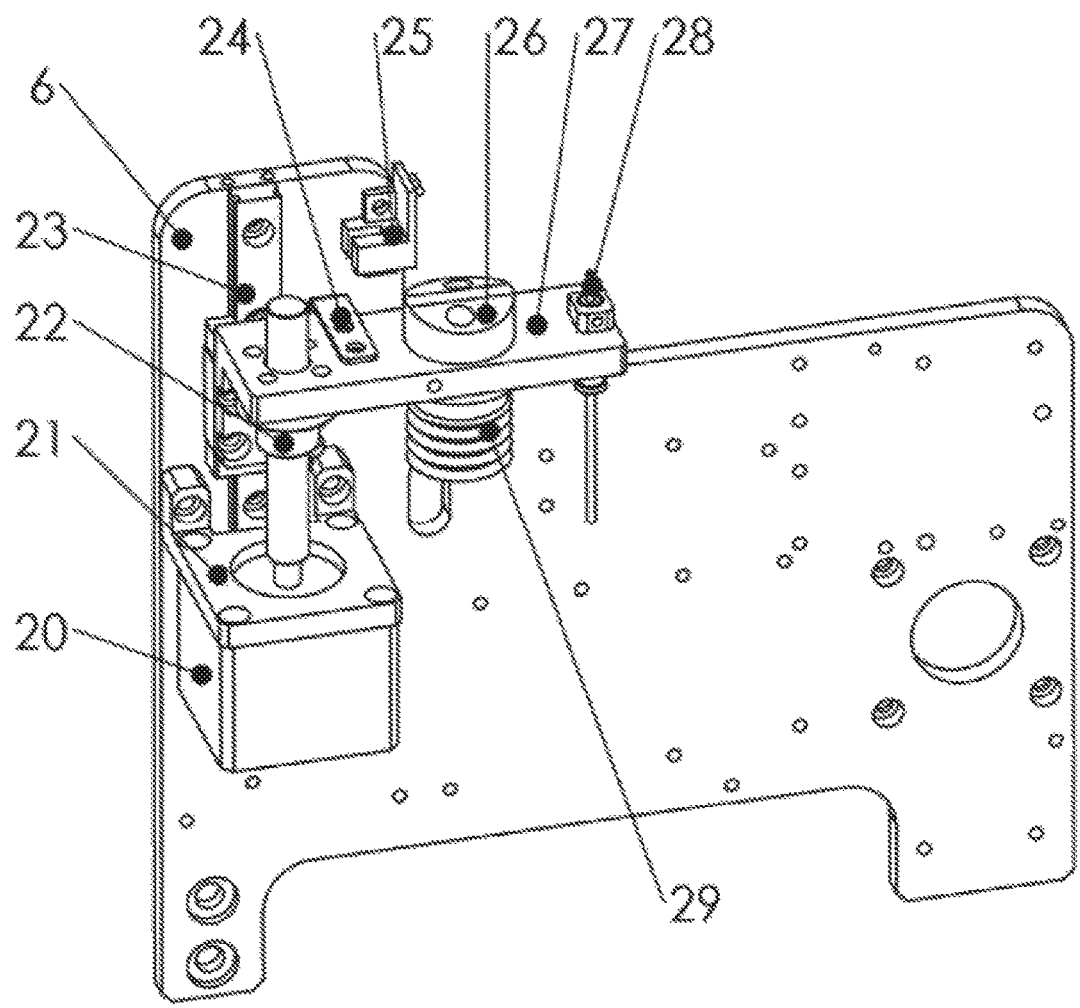
FIG. 5 shows the structure of the injector of the first embodiment example.

With particular reference to FIG. 5, the injector module 3 comprises a step motor 20, a motor stand 21, a feed screw nut 22, a linear slider 23, vertical home inducer 24, a home sensor 25, injection head 26, fixation footlock 27, extraction needle 28 and protective flexible bellow 29.

The step motor 20 is vertically installed on front side of the fixation vertical plate 6 with the motor stand 21, the thread spindle of the step motor 20 is inserted into the feed screw nut 22 fixed on the fixation horizontal footlock 27 connecting to the screw rod; the injection head 26, extraction needle 28 and vertical home inducer 24 are all installed on the fixation horizontal footlock 27, and the step motor 20 drives the fixation horizontal footlock 27 to move upward and downward; the home sensor 25 is installed on the fixation vertical plate 6 over the non-fixation end of the vertical home inducer 24.

When the vertical home inducer 24 goes upward to contact the home sensor 25, it triggers home signal. This position is the home position fixation horizontal footlock 27 for moving upward and downward.

When the fixation horizontal footlock 27 goes down, at the same time the linear sliding cartridge group 2 reaches the reading and injector position just behind the injection head 26. The injection head 26 comprises, in known per se technique, a number of injectors which penetrate the reading cup 12 from the top of the cup, protected by the protective flexible bellow 29 which adheres the upper side of the sliding cartridge 10, injecting a number of reagents in the cup: this way a light emission is generated from the cup, reflected by the reflector 11, reaching the Photomultiplier 50, through the hole 51, to allow to measure and count the photon emission by the reaction cup, in a known way.

After the reading step, the fixation horizontal footlock 27 goes up again to the home position, and the linear sliding cartridge group is shifted to the liquid extraction position, just behind the extraction needle 28. Then the fixation horizontal footlock 27 goes down again, the extraction needle 28 penetrates the reaction cup 12, to perform the liquid extraction from the cup. Then the fixation horizontal footlock 27 goes up again to the home position, and the linear sliding cartridge group 2 is shifted to the reaction cup releasing position.

The linear slider ensures consistency of the distance between the injection head and the fixation vertical plate during moving, and horizontal moving of the linear sliding cartridge mechanism mentioned above. Thus, consistency of relative position between the injection head and the reaction cup linear sliding cartridge is ensured; consistency of reaction cup liquid injection during injection is thus maximally enhanced, and thus counting consistency is guaranteed.

Therefore the shifting movements of the sliding cartridge module 2 and the injector module 3 are substantially reciprocally perpendicular.

Figure 6:
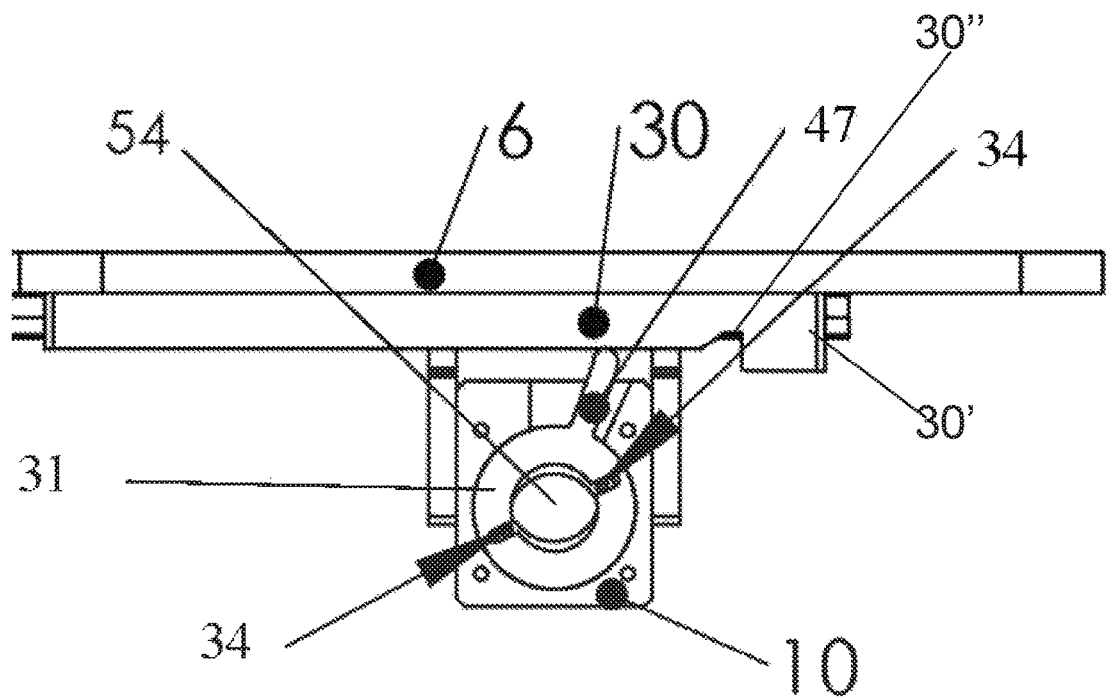
FIG. 6 is a first illustration of the shifting fork mechanism of the first embodiment example.
Figure 7:
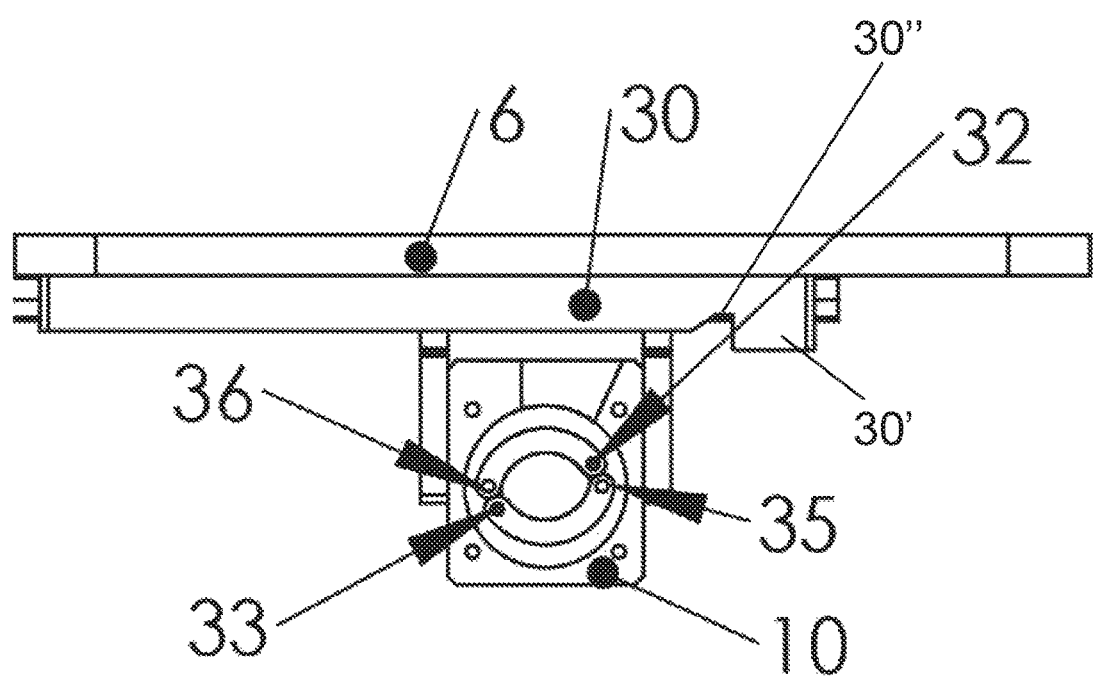
FIG. 7 is a second illustration of the shifting fork mechanism of the first embodiment example.

With particular reference to FIGS. 6 and 7, the shifting fork module 4 comprises a ring fork 31 and a sliding notched plate 30. The fork is installed at the top of the sliding cartridge 10, and the notched plate 30 is fixed on front side of the fixation vertical plate 6 and is parallel with the top of the sliding cartridge 10.

The shifting fork 4 comprises, further to said ring fork 31, two rotary paddles 32, 33, two rotary pins 36 and 35.

The ring fork 31 is composed of a ring-shaped part and a paddle 47, a radial stretched from the ring-shaped part. Moreover, at radial position of the ring-shaped part, linear grooves 34 are equipped symmetrically.

The ring fork sliding notched plate 30 is provided with raised edge 30' for blocking the paddle, and the raised edge 30' is located at the reaction cup releasing position on the linear slider 8.

The rotary paddles 32 and 33 are located right under the ring fork 31. The rotary pins 36 and 35 are installed on upper part of the sliding cartridge 10. One end of the rotary paddle 32 moves around the rotary pin 36 and one end of the rotary paddle 33 moves around the rotary pin 35.

Extruding free end of the rotary paddle 32 moves along line groove 34 of the ring shifting fork 31 and extruding free end of the rotary paddle 33 moves along another line groove 34 of the ring shifting fork 31.

When the ring fork 31 performs linear motion with the sliding cartridge 10, rotation is caused after the shifting fork contacting with the notch 30" in the sliding notched plate 30 to drive the rotary paddles 32 and 33 to move and to adjust size of inner bore 54 formed by the shifting fork.

Preferably at upper part the ring shifting fork 31 is equipped with sinker to prevent the ring shifting fork from popping. Near the fixation vertical plate on the top of the sliding cartridge 10, it is equipped with shifting fork limit slot. The shifting fork moves within the shifting fork limit slot.

Figure 8:
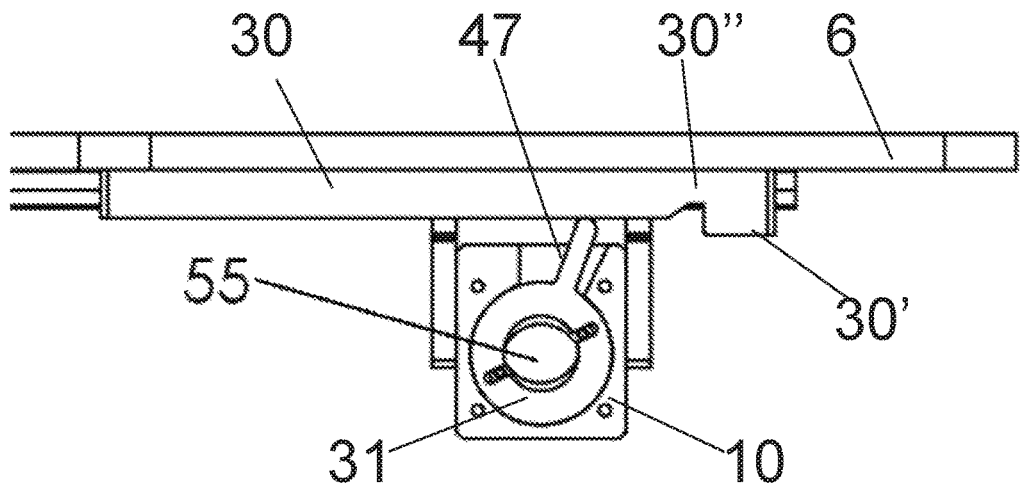
FIG. 8 is an illustration when the shifting fork supports the reaction cup of the first embodiment example.

With particular reference to FIG. 8, moving leftward and rightward of the sliding cartridge 10 drives the ring shifting fork 31 to slide on the sliding notched plate. When locating not at the notched position, the rotary paddle 32 forms a smaller inner bore 55 with the rotary paddle 33, and thus reaction cup edge is supported.

Figure 9:
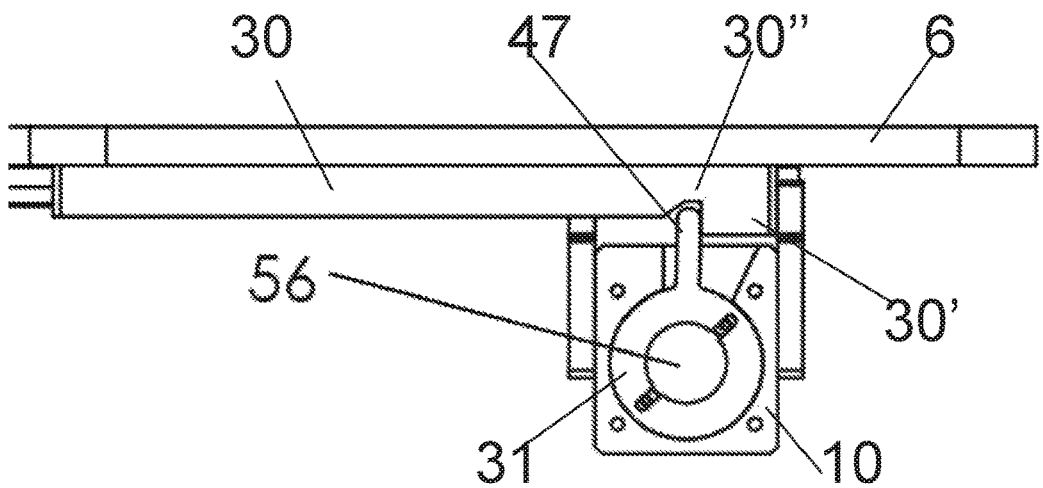
FIG. 9 is an illustration of the shifting fork to drop reaction cup of the first embodiment example.

With particular reference to FIG. 9, when the linear sliding cartridge 10 moves to the far right side, it brings the ring shift fork 31 to slide to the notch 30" of the sliding notched plate 30. The paddle 47 engages in the notch 30" and with raised edge 30' and makes it move counterclockwise. The rotary paddle 32 forms a larger inner bore 56 with the rotary paddle 33, thus the reaction cup can't be held, and drops freely.

As it appears from FIG. 4, the reaction cup has preferably a substantially cylindrical shape, and has a collar in the upmost position, having a larger diameter than that of the cup. The collar engages with the holding system described above, allowing supporting the cup when the inner bore is smaller, and releasing the cup when the inner bore becomes lager.

Figure 10:
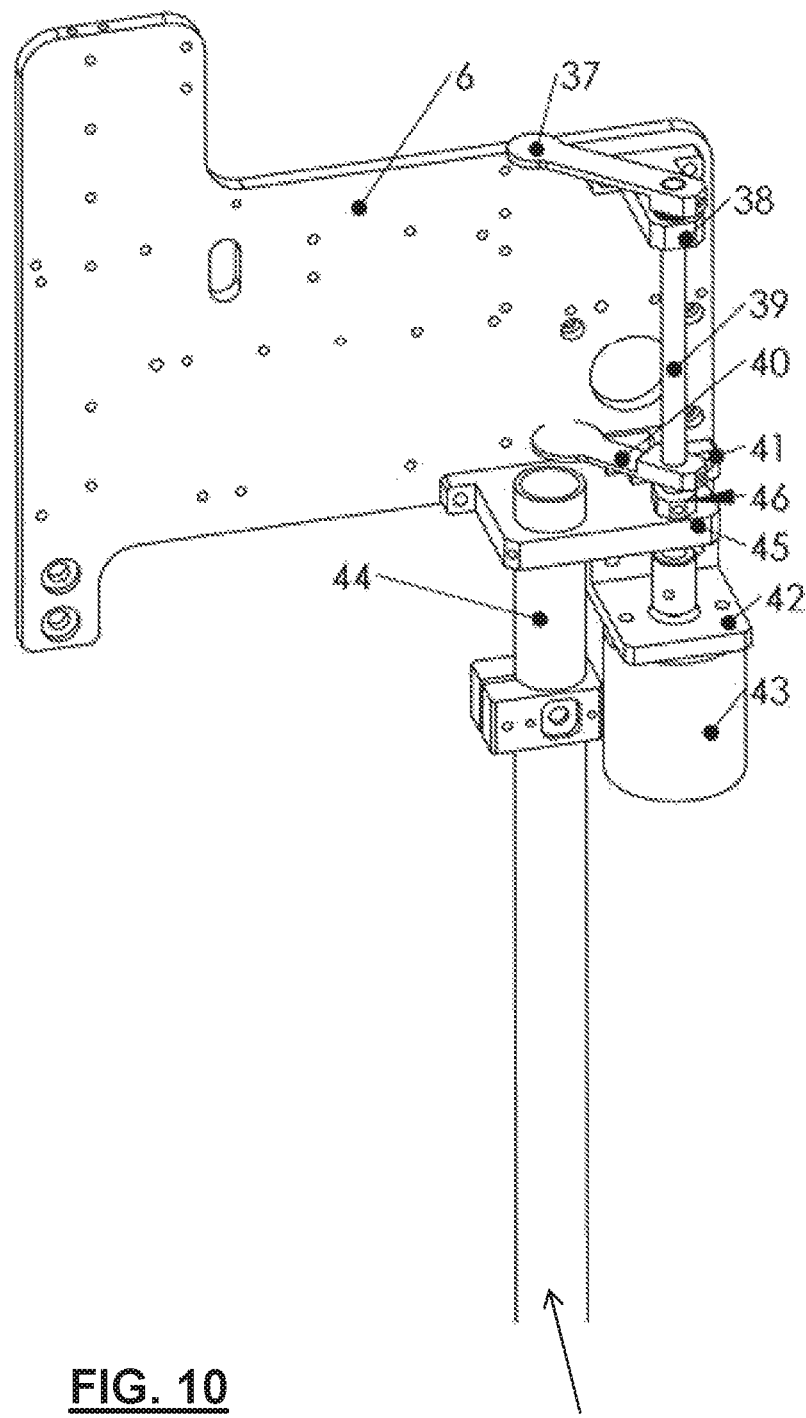
FIG. 10 shows structure of the light block mechanism of the first embodiment example.
Figure 11:
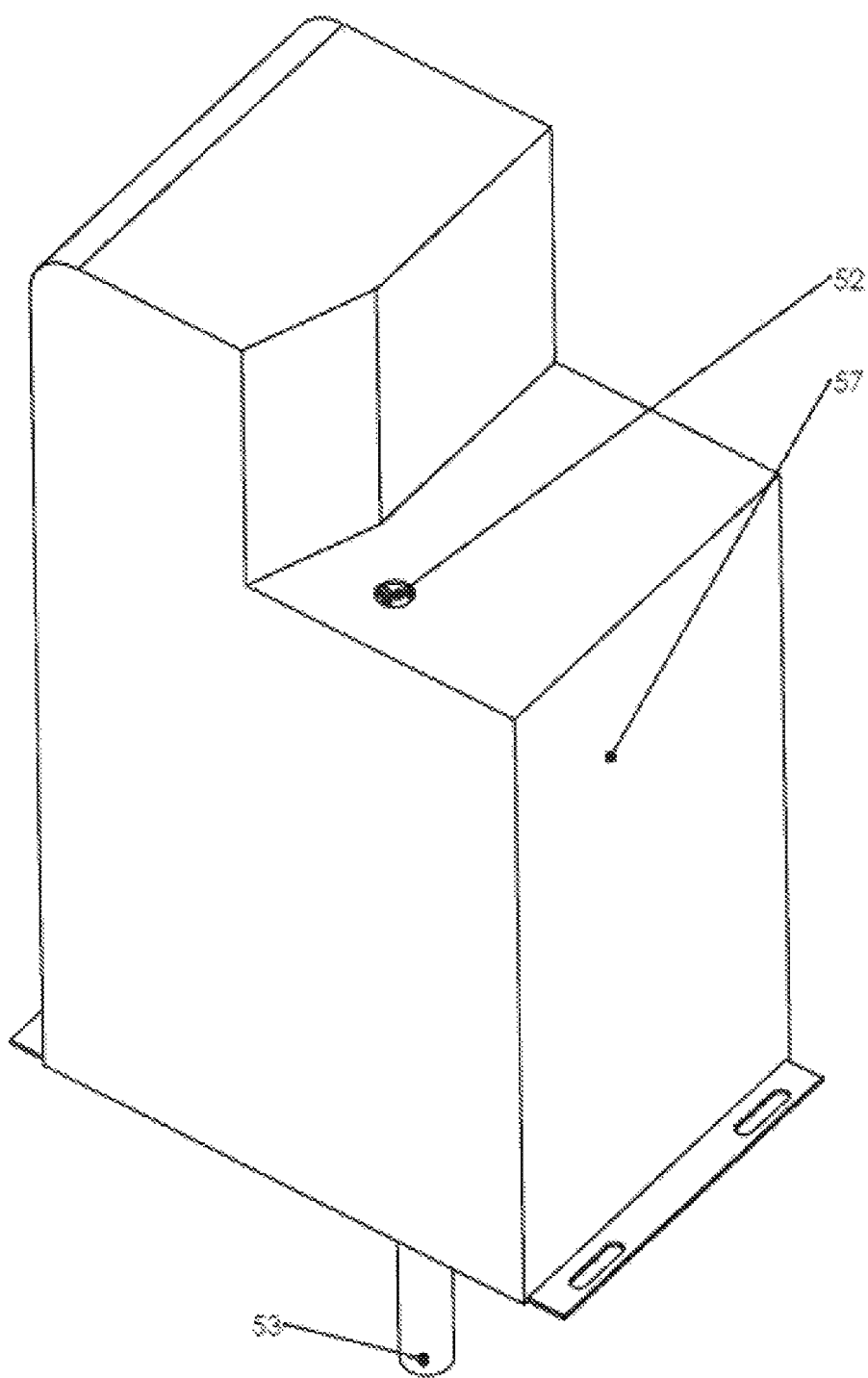
FIG. 11 is an appearance illustration of the overall module in the equipment of the first embodiment example.

With particular reference to FIG. 10, the light block module 5 comprises reaction cup placing hole light barrier 37, a rotary support 38, a rotary support 45, rotary axis 39, reaction cup releasing hole light barrier 40, rotation sensor 46, home sensor 41, motor stand 42 and brushless motor 43. The rotary axis is set vertically.

The rotary supports 38 and 45 and motor stand 42 are fixed on the fixation vertical plate 6. The rotary axis 39 connects with rotary axis of the brushless motor 43 for transmission. The reaction cup placing hole light barrier 37 and the reaction cup releasing hole light barrier 40 are fixed on the rotary axis, and the rotary sensor 46 is fixed on the rotary axis 39; the home sensor 41 is fixed on the fixation vertical plate; the rotary axis rotates to drive the rotary inducer 46 to rotate.

When the rotary inducer contacts the trigger home sensor 41 to send out home signal, rotary moving home is decided. Rotation position of the light block is controlled by emitting signal impulse, and light block is synchronously performed for both the reaction cup placing hole and reaction cup releasing hole.

The sliding of the cartridge module 2 and injector module 3 described above is preferably linear and reciprocally perpendicular (horizontal and vertical), notwithstanding the fact that other types of sliding are possible even not linear.

With reference to the FIGS. 12-20", a second non-limiting embodiment example of the fluorescence and/or chemiluminescence measuring device of the invention is shown, basically comprising all the modules of the first embodiment. In the FIGS. 12-20" all the elements marked with the same reference numbers as in the figures of the first embodiment, are the same elements of the first embodiment. In the following a description is given of the elements having a new reference number and replacing in part corresponding elements of the first embodiment, or having a different position.

Figure 12:
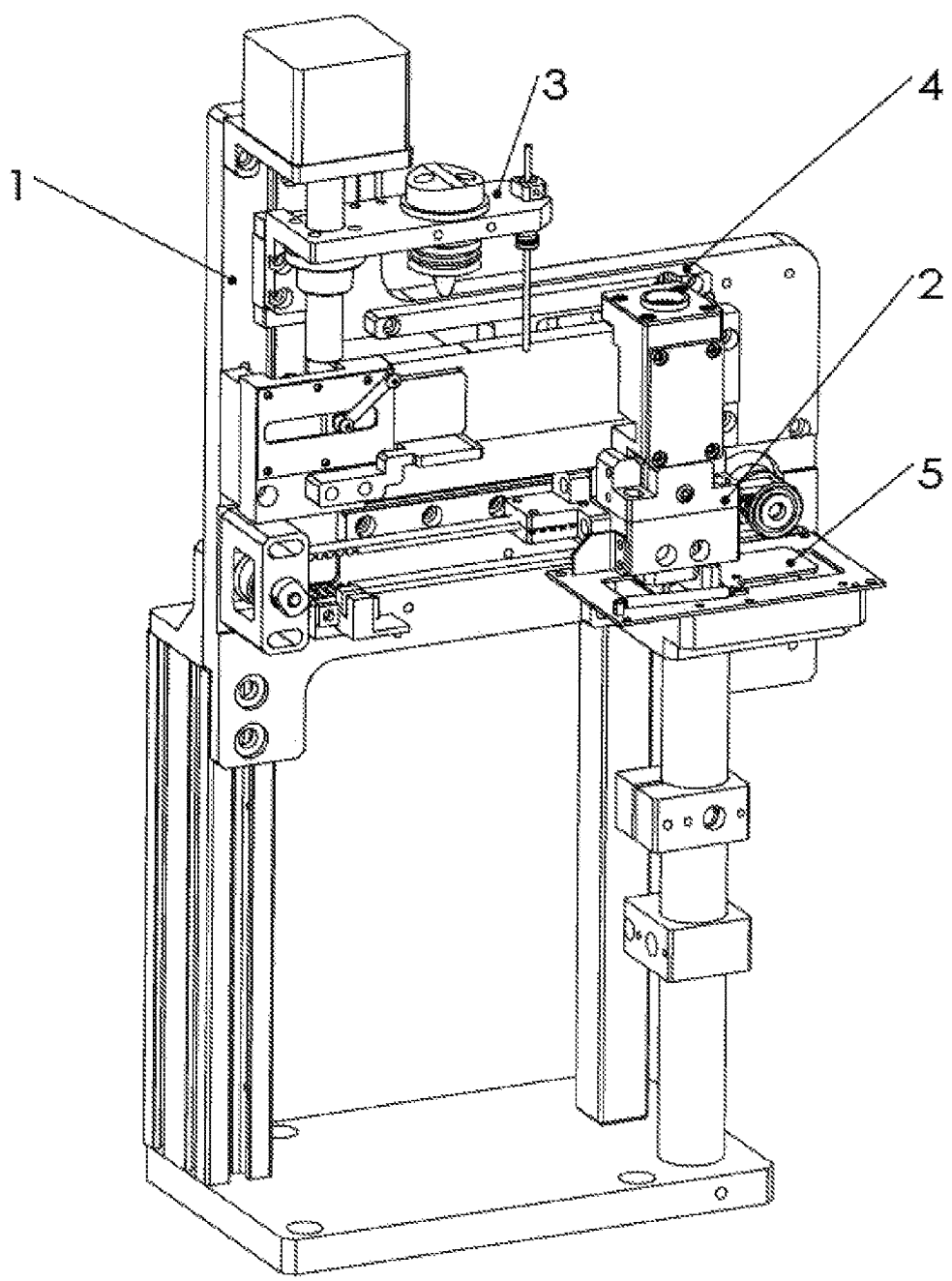
FIG. 12 shows a second embodiment example of internal structure of the device of this invention.
Figure 13:
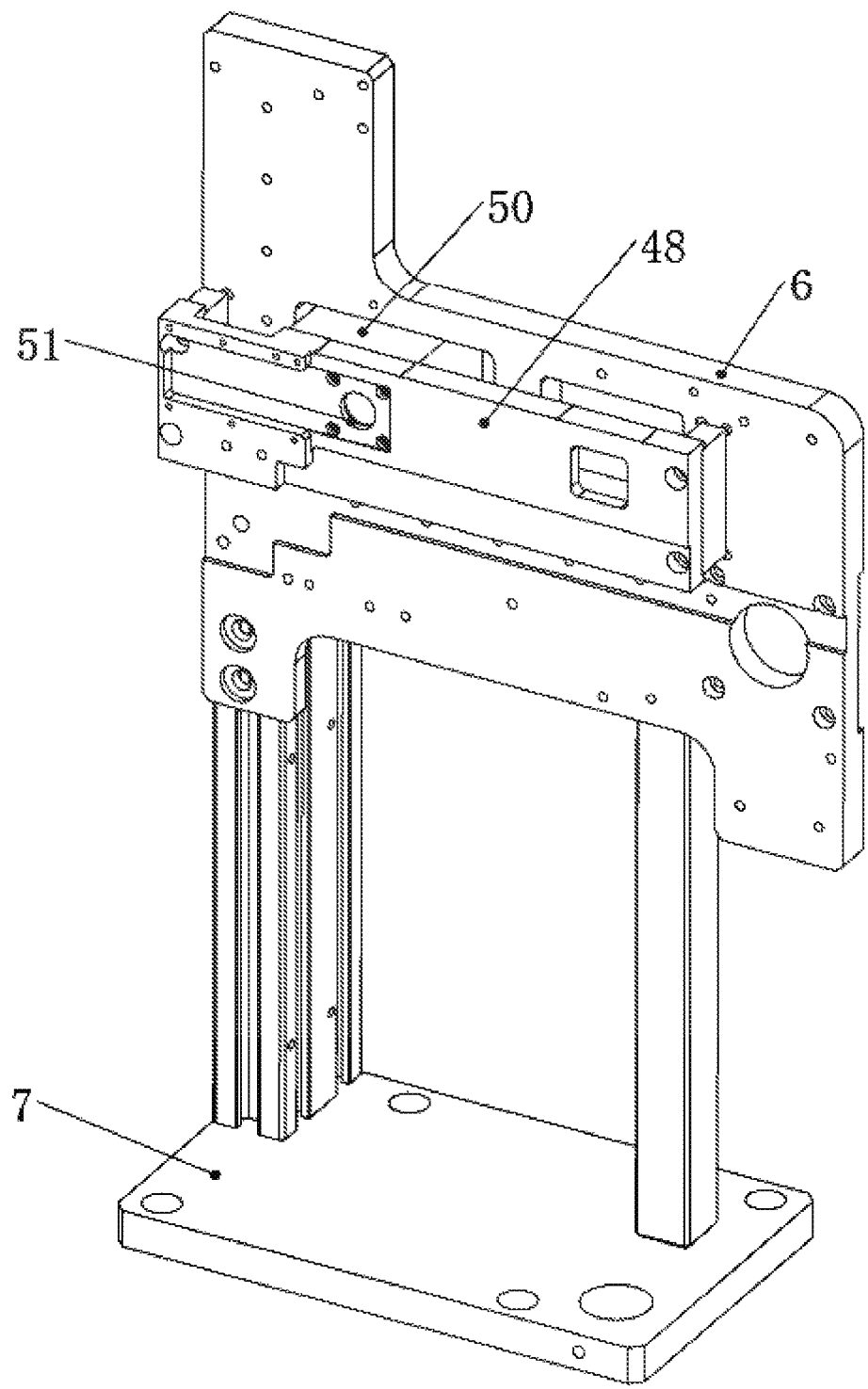
FIG. 13 shows installation of the photomultiplier of the second embodiment example.
Figure 14:
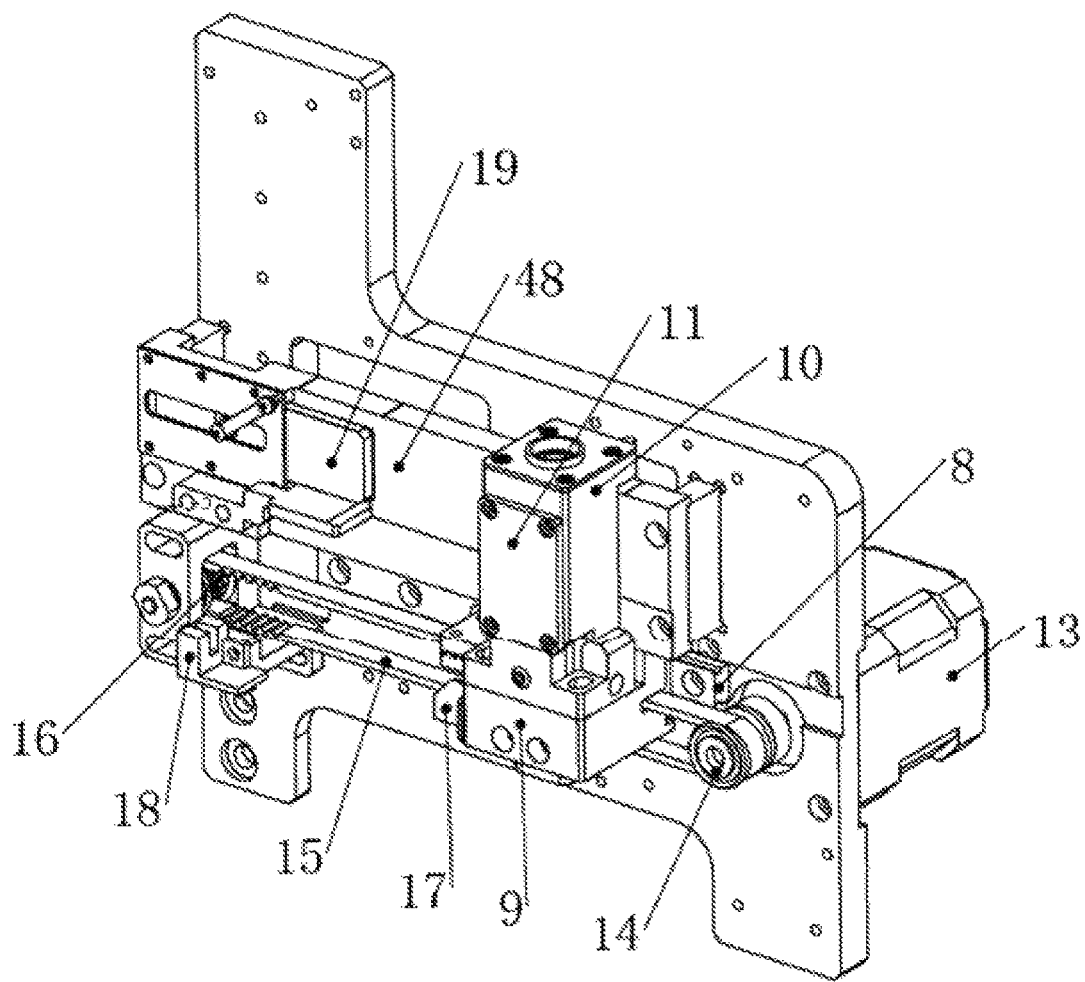
FIG. 14 shows a section of right view of the linear sliding cartridge mechanism of the second embodiment example.
Figure 16:
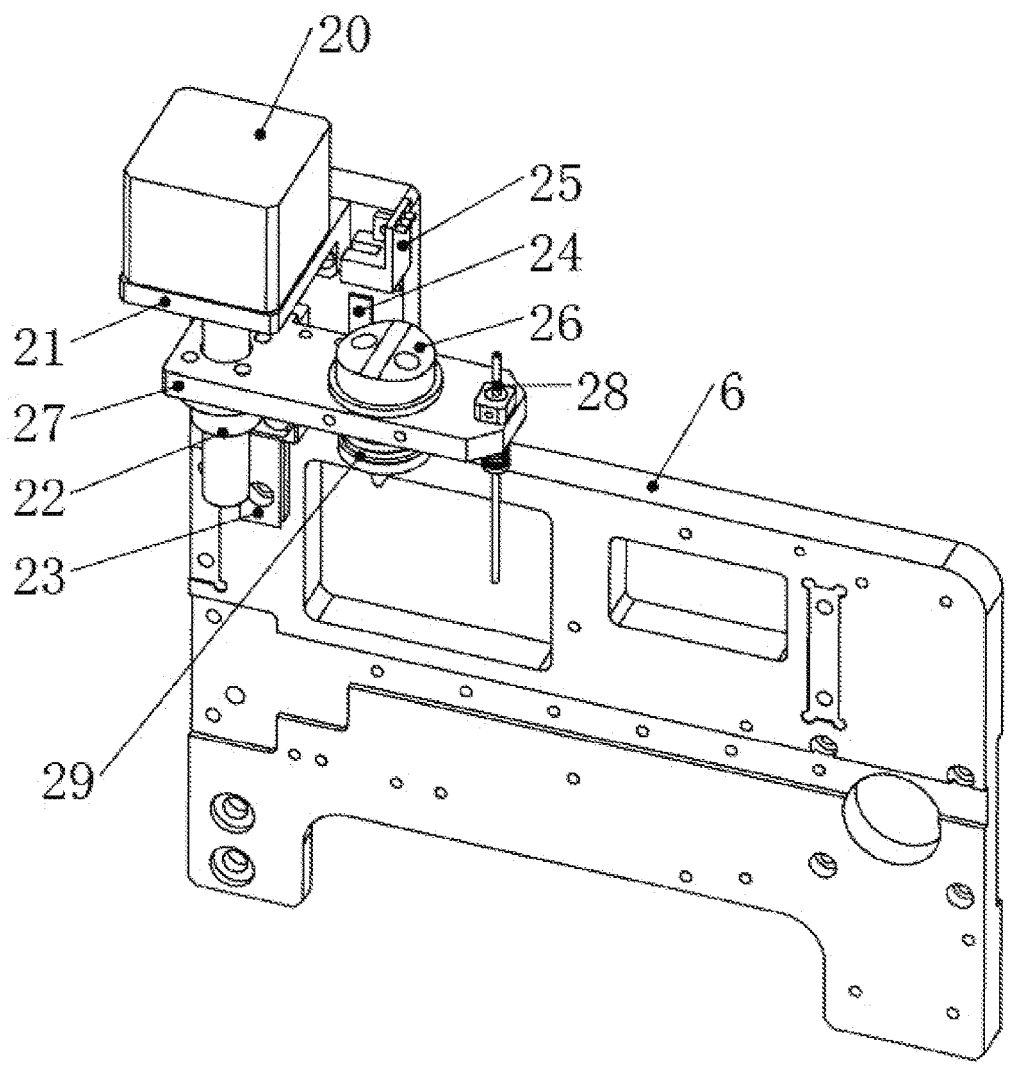
FIG. 16 shows the structure of the injector of the second embodiment example.

FIGS. 12, 16 show that the step motor 20 is placed above the linear slider 23, instead of below (as in FIGS. 1, 5 of the first embodiment), with the same way of working.

Figure 15:
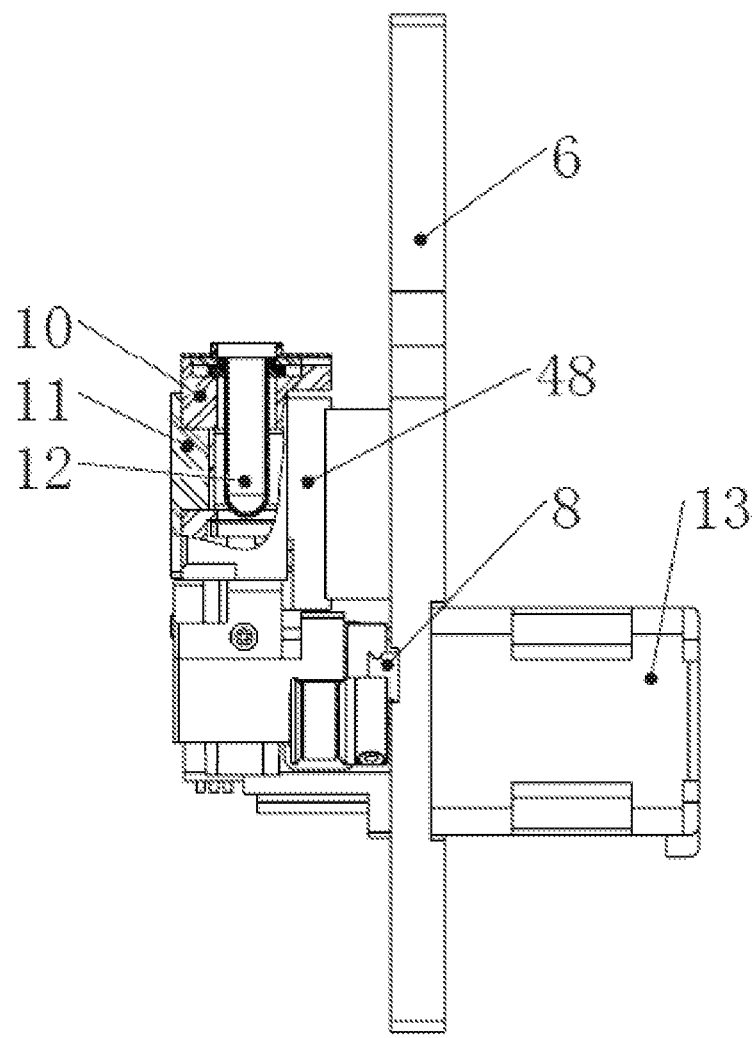
FIG. 15 is a right view of the linear sliding cartridge mechanism of the second embodiment example.

As described above for the first embodiment (FIG. 4), here it appears from FIG. 15 that the reaction cup has preferably a substantially cylindrical shape, and has a collar in the upmost position, having a larger diameter than that of the cup. The collar engages with the holding system described above, allowing supporting the cup when the inner bore is smaller, and releasing the cup when the inner bore becomes lager.

The light block unit 5 in the second embodiment is implemented by slider devices one as a light barrier for closing the placing reaction cup hole 52 (an example in FIG. 19'), the other (an example in FIG. 19") for closing the drop reaction cup hole (tube 44).

In the example of FIG. 19', the slider 73 has a raised edge 77 and a return spring 72 fixed also on the support 78, 79 of the slide. The slider normally closes the hole 52 (for example it is fixed to the shield overturned under the hole 52), and is shifted aside by the cartridge module 2 when reaching the position of placing reaction cup hole 52, opening the hole.

Equivalent considerations apply for the slider 61 of FIG. 19", spring 63, raised edge 62, fixed also on the support 64, 65 of the slide. The slider 61 normally closes the hole at the top of the tube 44 where it is fixed, and is shifted aside by the cartridge module 2 when reaching the position of drop reaction cup hole 44, opening the hole.

A fixed supporting structure 48 (FIGS. 13, 14, 17, 18) is placed between the ring fork sliding notched plate 30 and the sliding cartridge module 2. The photomultiplier 50 is fixed on the supporting structure 48 at the position of the hole 51 which is now present on the supporting structure 48, and the vertical plate 6 has a hole in correspondence with the photomultiplier 50 passing through the vertical plate 6.

Figure 20:
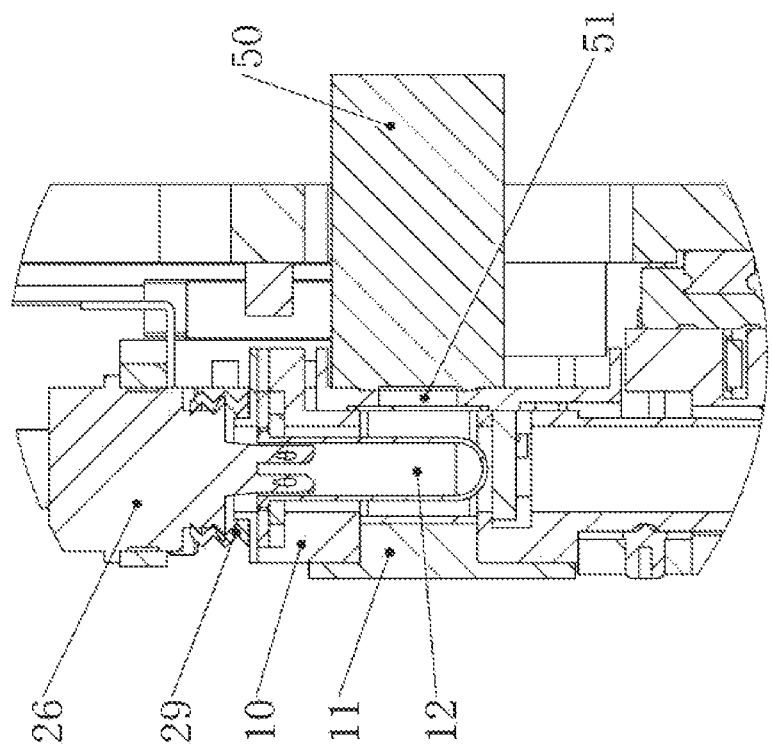
FIGS. 20', 20" show the structure of the linear sliding cartridge of the second embodiment example in the reading position and respective section.
Figure 20:
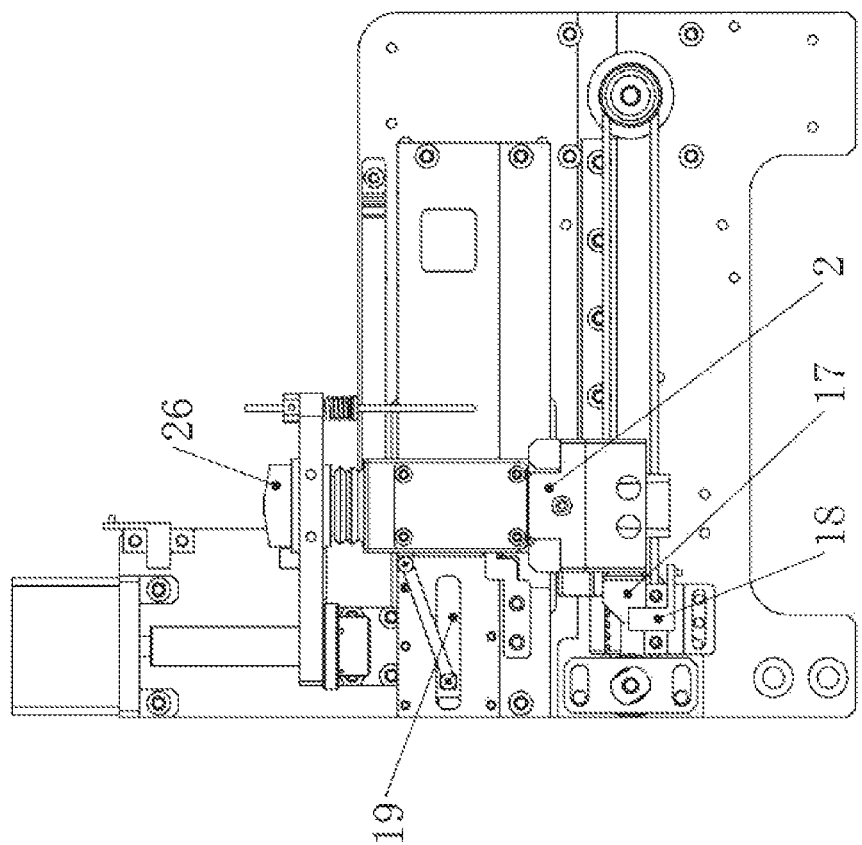

FIGS. 20', 20" show the linear sliding cartridge module 2 of the second embodiment example in the reading position and respective section. The injection head 26 is down on the reading cup 12, with injectors inside the top of the cup, generating the light emission which passes through the hole 51, also reflected by reflector 11, reaching the photomultiplier 50.

In the following a description of the method according to the invention is given.

The measuring method applies the new type of fluorescence and/or chemiluminescence measuring device, preferably of the first and second embodiment described above, taking use of the reading unit 1 formed by the photomultiplier fixed on the frame, the linear sliding cartridge 2 is driven by a step motor through the timing belt to repeatedly move leftward and rightward horizontally. In each cycle, it passes in turn through the reaction cup placing position, reading and injection position, extraction position and the reaction cup releasing position.

Measuring steps are as below:
(1) Circulation begins: the linear sliding cartridge module 2 moves to the reaction cup placing position, the shifting fork module 4 is always in a shut state. External equipment or operator places a reaction cup into the linear sliding cartridge module 2 through the hole 52, the reaction cup is supported by the shifting fork module 4 and held at upper part of the cartridge. The light block 5 is then closed, and the whole mechanism forms a dark room.
(2) The linear sliding cartridge module 2 equipped with reaction cup moves to the reading and injection position. The injector 3 is driven by screw rod to move downward to the position of the reaction cup. The injector 3 starts injection into the reaction cup. Meanwhile, the photomultiplier is activated, and reads optical signals generated during injection. At completion of reading, the injector 3 is driven by the screw rod to move upwards back to the initial position.
(3) The linear sliding cartridge module 2 equipped with reaction cup moves to the extraction position. The injector module 3 is driven by screw rod to move downward to the position of the reaction cup to extract liquid from the reaction cup, by the extraction needle 28. At completion of extraction, the injector module 3 is driven by the screw rod to move upwards back to the initial position.
(4) The sliding cartridge module 2 equipped with reaction cup moves to the reaction cup releasing position. At this time, the shifting fork module 4 is triggered, and the fork is stopped by the cam edge. Driven by the linear groove, the free end of the two rotary paddles move outwards; the inner bore 54 formed by the two rotary paddles is enlarged, the reaction cup freely drops into the reaction cup releasing tube 44 for taking back the reaction cup, and thus a fluorescent measuring is completed.

By means of the present invention, a number of advantages are achieved.

The device of the invention securely ensures fixed distance between the photomultiplier, and the linear guide rail structure of the sliding cartridge, and relative height of the photomultiplier and the reaction cup; and consistence of reading is well guaranteed. Moreover, the whole mechanism is enclosed in a dark shield, which maximally lowers background noise of the reading from the outside.

The whole device features simple structure, skillful design and easy control, allowing to get the outstanding features of the invention:

By fixation of the photomultiplier, and by taking use of linear guide rail structure of the linear sliding cartridge, the distance and relative height between the PMT and reaction cup are securely ensured; thus, consistence of reading is well guaranteed.

By skillfully taking use of movement of the ring fork in the shifting fork mechanism, the rotary paddles are driven to open and close for achieving reaction cup releasing and reaction cup placing. That greatly improves measuring speed and lowers work intensity of the operator;

Meanwhile, the mechanism is entirely enclosed in a dark shield, and that maximally lowers the background noise from the outside to the reading. With this method to measure fluorescence, the result of fluorescent measuring is accurate and measuring speed is improved for a certain level.

Many changes, modifications, variations and other uses and applications of the subject invention will become apparent to those skilled in the art after considering the specification and the accompanying drawings which disclose preferred embodiments thereof. All such changes, modifications, variations and other uses and applications which do not depart from the scope of the invention are deemed to be covered by this invention.

The elements and characteristics described in the various forms of preferred embodiments can be mutually combined without departing from the scope of the invention.

Further implementation details will not be described, as the man skilled in the art is able to carry out the invention starting from the teaching of the above description.

What is claimed is:

1. An apparatus configured for chemiluminescence and/or fluorescence measuring, comprising:
   a photomultiplier receiving and measuring chemiluminescence and/or fluorescence of a photo-emission emitted from a single reaction cup;
   a sliding cartridge containing said single reaction cup and adapted to slide in a first sliding direction;
   a first slider sliding said sliding cartridge in said first sliding direction to locate said single reaction cup at each of the following positions:
   a reaction cup placing position,
   a reading and injector position, and
   a liquid extraction position and,
   a reaction cup releasing position;
      an injector sliding in a second sliding direction substantially perpendicular to said first sliding direction;
      a second slider sliding said injector in said second sliding direction to a position wherein said injector:
      injects reaction agents into said single reaction cup when said sliding cartridge is in said reading and injector position, and extracts liquid from said single reaction cup when said sliding cartridge is in said liquid extraction position;
      a shifting fork moving linearly along said first sliding direction from being in a shut state wherein the shifting fork holds said single reaction cup in said sliding cartridge to being in an open state wherein shifting fork lets said single reaction cup to drop from said sliding cartridge into a reaction cup releasing tube when said sliding cartridge is reaching said reaction cup releasing position;
   an enveloping shield enveloping said apparatus completely and comprising:
      a first hole letting said single reaction cup to enter said sliding cartridge when said sliding cartridge is in said reaction cup placing position, and
      a second hole letting said single reaction cup to drop into the reaction cup releasing tube when said sliding cartridge is in said reaction cup releasing position; and
      a light blocker closing said first hole and second hole when said sliding cartridge is neither in said reaction cup placing position nor in said reaction cup releasing position.

2. The apparatus as in claim 1, wherein said first slider is fixed on a support in the apparatus, and comprises:
   a timing belt and a first motor causing said sliding cartridge to slide;
   a first support supporting said sliding cartridge; and
   a first home sensor to sense said reaction cup releasing position.

3. The apparatus as in claim 1, wherein said injector comprises:
   an injection head and an extraction needle;
   injectors in said injection head to inject reagents into said single reaction cup when in said reading and injector position;
   said extraction needle to extract liquid from said single reaction cup when in said liquid extraction position;
   a protective flexible bellow closing the interspace between the sliding cartridge and the injection head when in said reading and injector position; and
   a fixation footlock supporting said injection head, protective flexible bellow, extraction needle and cooperating with said second slider.

4. The apparatus as in claim 1, wherein said second slider is fixed on a support in the apparatus, and comprises:
   a second motor causing said injector to slide; and
   a second support supporting said injector.

5. The apparatus as in claim 1, wherein said shifting fork comprises a width adjuster of an inner bore in which said single reaction cup is inserted at the reaction cup placing position, so as to hold said single reaction cup when said width is smaller, or the let said reaction cup drop, when said width is larger.

6. The apparatus as in claim 1, wherein said light blocker comprises a first light barrier and a second light barrier, and a rotator to cause said first light barrier to rotate so as to close or open said first hole, and to cause said second light barrier to rotate so as to close or open said second hole.

7. The apparatus as in claim 1, wherein said light blocker comprises a first slider and a second slider, and a third slider to cause said first slider to slide so as to close or open said first hole, and to cause said second slider to slide so as to close or open said second hole.

8. The apparatus as in claim 1, wherein said sliding cartridge contains said single reaction cup and cooperates with said first slider, and comprises a reflector for reflecting light emitted by said single reaction cup towards said photomultiplier.

9. The apparatus as in claim 1, further comprising a third hole in a support through which the photo-emission of said single reaction cup is passed to said photomultiplier.

10. A method for chemiluminescence and/or fluorescence measuring, using the apparatus as in claim 1, comprising the following steps in succession:

moving linearly along a sliding direction the sliding cartridge to the single reaction cup placing position, the shifting fork being in a shut state;

placing the single reaction cup into the sliding cartridge through the first hole, the single reaction cup being supported by the shifting fork;

closing the light blocker, forming a dark room;

moving linearly along said sliding direction the sliding cartridge to the reading and injection position;

moving the injector downwards to the single reaction cup, where the injector starts an injection into the single reaction cup;

activating the photomultiplier, so as to read the photo-emission during the injection;

at completion of reading, driving the injector upwards back to a home position;

moving linearly along said sliding direction the sliding cartridge to the extraction position;

moving the injector downwards to the reaction cup to extract liquid from the single reaction cup;

at completion of extraction, driving the injector to move upwards back to the home position;

moving linearly along said sliding direction the sliding cartridge to the reaction cup releasing position; and triggering the shifting fork to an open state, so as the reaction cup freely drops.

* * * * *